US00PP15973P2

(12) United States Plant Patent
Vester

(10) Patent No.: US PP15,973 P2
(45) Date of Patent: Sep. 20, 2005

(54) ***ECHINACEA* PLANT NAMED 'LITTLE MAGNUS'**

(50) Latin Name: *Echinacea purpurea*
Varietal Denomination: Little Magnus

(75) Inventor: Mart Vester, Zwaanshoek (NL)

(73) Assignee: Green Works, International, 't Zand (NL)

( * ) Notice: Subject to any disclaimer, the term of this patent is extended or adjusted under 35 U.S.C. 154(b) by 33 days.

(21) Appl. No.: 10/878,564

(22) Filed: Jun. 28, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Echinacea* plant named 'Little Magnus', characterized by its compact growth habit; rapid growth rate; red purple-colored ray florets; horizontally-orientated ray florets; long and continuous flowering period; and good garden performance.

1 Drawing Sheet

Botanical classification/cultivar designation: *Echinacea purpurea* cultivar Little Magnus.

BACKGROUND OF THE INVENTION

The present Invention relates to a new and distinct cultivar of *Echinacea* plant, botanically known as *Echinacea purpurea,* and hereinafter referred to by the name 'Little Magnus'.

The new *Echinacea* is a product of a planned breeding program conducted by the Inventor in Zwaanshoek, The Netherlands. The objective of the breeding program is to develop new compact *Echinacea* cultivars with horizontal ray florets.

The new *Echinacea* originated from a self-pollination made by the Inventor in 1995 of an unnamed *Echinacea purpurea* selection, not patented. The new *Echinacea* was discovered and selected as a single flowering plant by the Inventor in a controlled environment in Zwaanshoek, The Netherlands in 1997 from the resultant progeny of the self-pollination. The new *Echinacea* was selected on the basis of its compact growth habit, attractive ray and disc floret coloration and horizontal ray florets.

Asexual reproduction of the new *Echinacea* by divisions was first conducted in Zwaanshoek, The Netherlands in 1999. Since then, asexual reproduction by divisions has shown that the unique features of this new *Echinacea* are stable and reproduced true to type in successive generations.

SUMMARY OF THE INVENTION

The cultivar Little Magnus has not been observed under all possible environmental conditions. The phenotype may vary somewhat with variations in environment such as temperature and light intensity without, however, any variance in genotype.

The following traits have been repeatedly observed and are determined to be the unique characteristics of 'Little Magnus'. These characteristics in combination distinguish 'Little Magnus' as a new and distinct *Echinacea:*

1. Compact growth habit.
2. Rapid growth rate.

3. Red purple-colored ray florets.
4. Horizontally-orientated ray florets.
5. Long and continuous flowering period.
6. Good garden performance and tolerance to wind and rain.

Plants of the new *Echinacea* differ primarily from plants of the parent selection in growth habit and ray floret coloration.

Plants of the new *Echinacea* can be compared to plants of the *Echinacea* cultivar Magnus, not patented. In side-by-side comparisons conducted in Zwaanshoek, The Netherlands, plants of the new *Echinacea* differed from plants of the cultivar Magnus in the following characteristics:

1. Plants of the new *Echinacea* were more compact than plants of the cultivar Magnus.
2. Ray florets of plants of the new *Echinacea* were horizontal-oriented whereas ray florets of plants of the cultivar Magnus were upright.
3. Ray florets of plants of the new *Echinacea* were darker in color than ray florets of plants of the cultivar Magnus.

Plants of the new *Echinacea* can also be compared to plants of the *Echinacea* cultivar Kim's Knee High, not patented. In side-by-side comparisons conducted in Zwaanshoek, The Netherlands, plants of the new *Echinacea* differed from plants of the cultivar Kim's Knee High in the following characteristics:

1. Ray florets of plants of the new *Echinacea* were horizontally-orientated whereas ray florets of plants of the cultivar Kim's Knee High were upright.
2. Ray florets of plants of the new *Echinacea* were darker in color than ray florets of plants of the cultivar Kim's Knee High.

BRIEF DESCRIPTION OF THE PHOTOGRAPHS

The accompanying colored photographs illustrate the overall appearance of the new *Echinacea* showing the colors as true as it is reasonably possible to obtain in colored reproductions of this type. Colors in the photographs may differ from the color values cited in the detailed botanical description which accurately describe the colors of the new *Echinacea*.

The photograph at the top of the sheet comprises a top perspective view of a typical flowering plant of 'Little Magnus' grown in an outdoor nursery.

The photograph at the bottom of the sheet is a close-up view of a typical inflorescence of 'Little Magnus'.

DETAILED BOTANICAL DESCRIPTION

The aforementioned photographs and following observations and measurements describe plants grown in 't Zand, The Netherlands, in an outdoor nursery under full sun conditions during the spring. When the plants were about one year old, the photographs and the observations and measurements were taken. Plants used for the detailed description were grown in 15-cm containers. During this time, day temperatures ranged from 5 to 20° C. and night temperatures ranged from 2 to 12° C. Color references are made to The Royal Horticultural Society Colour Chart, 1995 Edition, except where general terms of ordinary dictionary significance are used.

Botanical classification: *Echinacea purpurea* cultivar Little Magnus.

Parentage: An unnamed *Echinacea purpurea* selection.

Propagation:

*Type.*—By divisions.

*Time to initiate roots, summer.*—About three weeks at 18° C.

*Time to initiate roots, winter.*—About five weeks at 18° C.

*Time to produce a rooted plant, summer.*—About four weeks at 18° C.

*Time to produce a rooted plant, winter.*—About six weeks at 18° C.

*Root description.*—Fine, fibrous and well-branched.

Plant description:

*Appearance.*—Perennial herbaceous container and garden plant. Upright and compact plant habit; inverted triangle. Freely basally branching; about 40 basal branches per plant. Moderately vigorous; rapid growth rate.

*Plant height.*—About 35 cm.

*Plant width or area of spread.*—About 40 cm.

*Basal branches.*—Length: About 35 cm. Diameter: About 4 mm. Aspect: Mostly upright. Strength: Strong. Texture: Smooth. Color: 144B with longitudinal stripes, 185A.

*Foliage description.*—Arrangement: Alternate; single. Length: About 10 to 18 cm. Width: About 4 to 6 cm. Shape: Lanceolate. Apex: Acuminate. Base: Attenuate. Margin: Serrate. Venation pattern: Parallel. Texture, upper and lower surfaces: Pubescent; scabrous. Color: Developing and fully expanded foliage, upper surface: 136A. Developing and fully expanded foliage, lower surface: 138A. Venation, upper and lower surfaces: 145C. Petiole: Length: About 2 cm. Diameter: About 5 mm. Texture, upper and lower surfaces: Smooth. Color, upper and lower surfaces: 145C overlain with 183B.

Inflorescence description:

*Appearance.*—Terminal inflorescences held mostly above and beyond the foliage on strong peduncles. Composite inflorescence form, radially symmetrical; oblanceolate-shaped ray florets; disc florets massed at the center; ray and disc florets develop acropetally on the receptacle. Inflorescences persistent. Inflorescences face mostly upright.

*Time of flowering.*—Long flowering period; plants flower freely during the early summer and continue to flower continuously through the fall in 't Zand, The Netherlands.

*Postproduction longevity.*—Inflorescences maintain good color and substance for about three or four weeks on the plant.

*Quantity of inflorescences.*—One inflorescence per stem; about 40 inflorescences in flower at one time per plant.

*Fragrance.*—Not detected.

*Inflorescence bud.*—Length: About 5 cm. Diameter: About 7.5 cm. Shape: Roughly spherical. Color: 143A.

*Inflorescence size.*—Diameter: About 15 cm. Depth (height): About 5 cm. Disc diameter: About 5 cm.

*Ray florets.*—Length: About 5 cm. Width: About 1.5 cm. Shape: Oblanceolate. Apex: Obtuse to acute. Base: Attenuate. Margin: Entire. Texture, upper and lower surfaces: Smooth. Orientation: Initially upright then horizontal, perpendicular to the peduncle. Number of ray florets per inflorescence: About 25 to 30 in a single whorl. Color: When opening and fully opened, upper surface: 58A. When opening, lower surface: 64B.

*Disc florets.*—Shape: Elongated. Apex: Five-pointed; acute. Length: About 2 cm. Width: About 2 mm. Number of disc florets per inflorescence: Numerous. Color: Apex: 180B. Mid-section: Close to 144B. Base: Close to 155D.

*Phyllaries.*—Quantity per inflorescence: About 25 to 58. Length: About 2 cm. Diameter: About 5 mm. Shape: Lanceolate. Apex: Acute. Base: Fused to receptacle. Margin: Entire. Texture, upper and lower surfaces: Pubescent. Color, upper and lower surfaces: 143A.

*Reproductive organs.*—Androecium: Present on disc florets only. Stamen number: About six per floret; basifixed. Anther shape: Narrowly oblong. Anther length: About 2 mm. Anther color: 1D. Pollen amount: Moderate. Pollen color: 7B. Gynoecium: Present on both ray and disc florets. Pistil number: One per floret. Pistil length: About 5 mm. Stigma shape: Two-parted. Stigma color: Close to 6A. Style length: About 4 mm. Style color: Close to 155D.

*Seed.*—Length: Less than 5 mm. Diameter: Less than 2 mm. Color: Medium tan.

Disease/pest resistance: Resistance to pathogens and pests common to *Echinaceas* has not been observed on plants grown under outdoor conditions.

Garden performance: Plants of the new *Echinacea* have been observed to have good garden performance and to tolerate wind and rain. Plants of the new *Echinacea* have been observed to be winter hardy in 't Zand, The Netherlands.

It is claimed:

1. A new and distinct cultivar of *Echinacea* plant named 'Little Magnus', as illustrated and described.

* * * * *

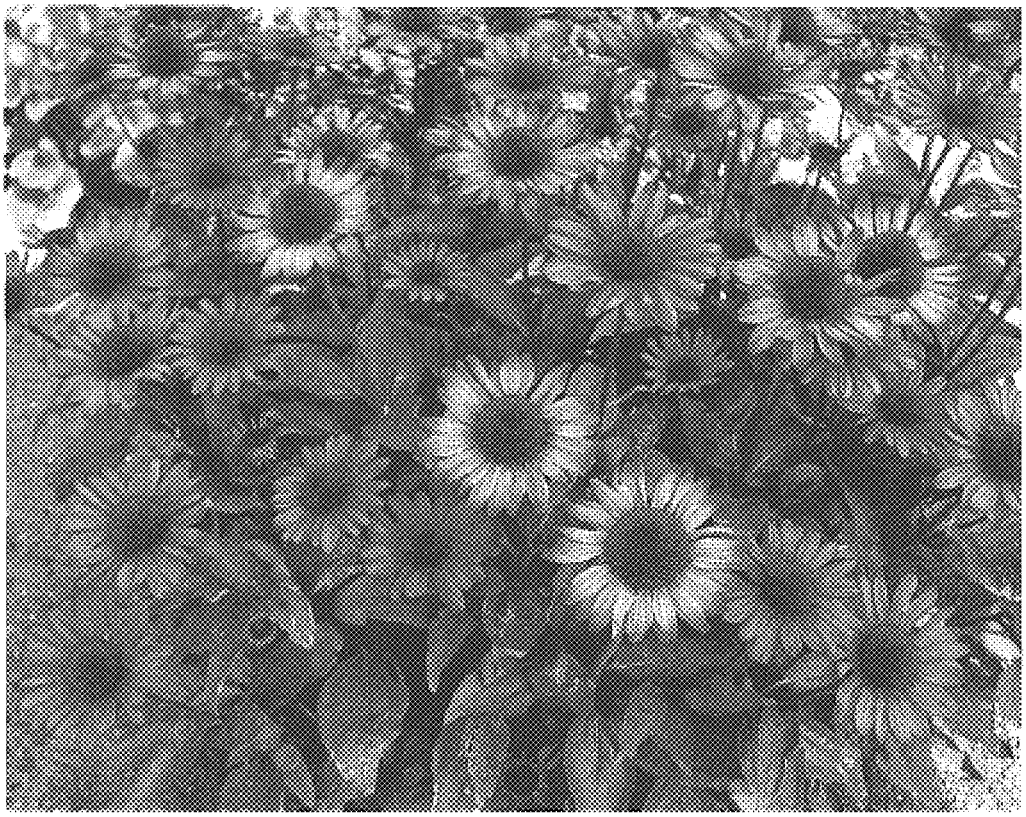
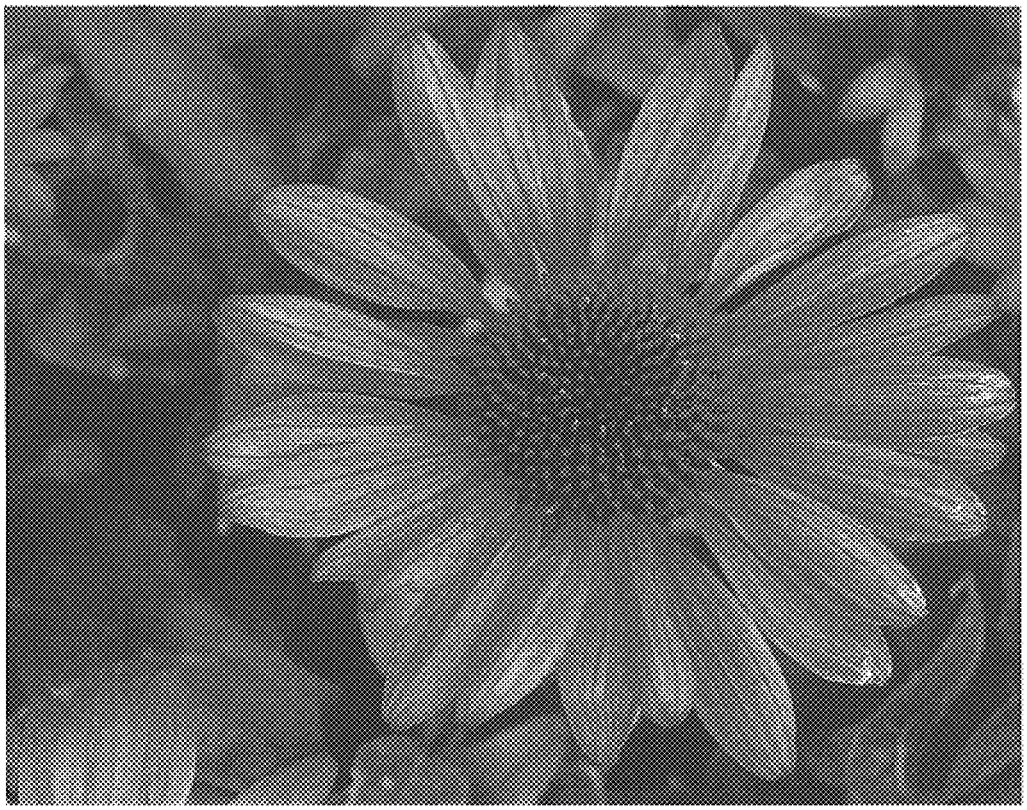
Little Magnus